United States Patent [19]

Kurihara et al.

[11] Patent Number: 5,039,699

[45] Date of Patent: Aug. 13, 1991

[54] ANTI-PEPTIC ULCER AGENT

[75] Inventors: Masaaki Kurihara; Keiichiro Ohta, both of Saitamaken, Japan

[73] Assignee: Lederle (Japan), Ltd., Tokyo, Japan

[21] Appl. No.: 329,230

[22] Filed: Mar. 27, 1989

[51] Int. Cl.$^5$ .................. A61K 31/355; A61K 31/375
[52] U.S. Cl. ................................. 514/458; 514/474; 514/925; 514/926; 514/927; 514/928
[58] Field of Search .............. 514/458, 925, 926, 927, 514/474, 458, , 928

[56] References Cited

U.S. PATENT DOCUMENTS

| | | | |
|---|---|---|---|
| 3,878,202 | 4/1975 | Fukawa et al. | 424/284 |
| 4,221,810 | 9/1980 | Tahara et al. | 424/284 |
| 4,320,141 | 3/1982 | Komatsu et al. | 424/284 |

FOREIGN PATENT DOCUMENTS

| | | |
|---|---|---|
| 15429 | 2/1978 | Japan . |
| 60-26770 | 6/1985 | Japan . |

OTHER PUBLICATIONS

Hilton J. E. and Summers M.P. "The Effect of . . . ", Int. J. Pharm. 32 13–19 (1986).

Primary Examiner—C. Warren Ivy
Assistant Examiner—Celia Chang
Attorney, Agent, or Firm—Wegner, Cantor, Mueller & Player

[57] ABSTRACT

An anti-peptic ulcer agent comprising (a) a powdery material which includes tocopheryl retinoate, light silicic anhydride, and an antioxidant; (b) a low substituted hydroxypropylcellulose; and (c) polyvinylpyrrolidone which is orally administrable.

10 Claims, 2 Drawing Sheets

ANTI-PEPTIC ULCER AGENT

It is known that tocopheryl retinoate is an ester originating from α-tocopherol and vitamin A acid. It aids in the prevention of skin degradation and in curing peptic ulcer by increasing submucosal and mucosal growth.

Attempts have been previously made to provide preparations of tocopheryl retinoate using powderization methods. These methods including powderizing by means of adsorption on a pharmaceutically acceptable adhesive agent such as silicic anhydride, or by means of the spray dry method. Tablets are then prepared from the powdery material, or hard capsules are prepared from soft capsules, upon admixture with an appropriate oily substance. It is to be noted, however, that a disadvantage of these preparation is that the active ingredient, tocopheryl retinoate, cannot adequately adhere to ulcer lesions when orally administered. Thus, these preparations fail to effectively exhibit the tissue growth activity inherent in tocopheryl retinoate.

SUMMARY OF THE INVENTION

The present invention provides an anti-ulcer agent containing tocopheryl retinoate as an active ingredient. More particularly, the present invention is concerned with an anti-peptic ulcer agent prepared from a formulation adapted so as to effectively exhibit anti-peptic ulcer activity which is inherent in its active ingredient, tocopheryl retinoate. This active ingredient also exhibits a potent tissue growth activity on submucosa and mucosa.

In accordance with the invention, there is provided an anti-peptic ulcer composition for topical delivery of tocopheryl retinoate to the ulcerated lesion in the gastrointestinal tract which permits the tocopheryl retinoate to remain at said lesion for a prolonged period of time. The anti-ulcer composition comprises a powdery mixture containing:

(a) from about 0.05 to about 60 parts by weight tocopheryl retinoate adsorbed on silicic anhydride having an average diameter of up to about 3.0 microns, which is referred to herein as light silicic anhydride;

(b) from about 5 to about 20 parts by weight hydroxypropylcellulose; and (c) from about 2 to about 15 parts by weight polyvinylpyrrolidone having a molecular weight of from about 30,000 to about 40,000;

whereby the tocopheryl retinoate remains in contact with said lesion for a prolonged period of time, and the tocopheryl retinoate is permitted to work directly on said lesion for said prolonged period of time. The hydroxypropylcellulose now available and thus preferred contain not less than 5.0 percent and not more than 16.0 percent of hydroxypropoxy groups, which is calculated on the dry weight basis.

Thus, the tocopheryl retinoate contacts said lesion:
(1) to expedite the formation of muscle layer of said lesion, and
(2) to promote the formation of thick mucosal layer for protecting from gastric acid,
for a prolonged period of time.

In a preferred embodiment, the anti-peptic ulcer composition is in the form of a powder.

In a further preferred embodiment, the anti-peptic ulcer composition is in the form of a tablet.

In a further preferred embodiment, the anti-peptic ulcer composition is in the form of a capsule.

In a further preferred embodiment, the anti-peptic ulcer composition comprises granules of said anti-ulcer composition.

In a preferred embodiment, there is provided an anti-peptic ulcer composition wherein the amount of tocopheryl retinoate contained in the component (a) is from about 30 to about 60 percent by weight of the total amount of tocopheryl retinoate and said light silicic anhydride.

In accordance with a second aspect of the invention, there is provided an anti-peptic ulcer composition capable of delivering tocopheryl retinoate to the ulcerated lesion the stomach wall whereby said tocopheryl retinoate is retained directly on said lesion for a prolonged period of time. The tocopheryl retinoate is in a powdery form intimately associated with (a) a light silicic anhydride on which said tocopheryl retinoate is adsorbed; (b) a hydroxypropylcellulose; and (c) a polyvinylpyrrolidone. The hydroxypropylcellulose and said polyvinylpyrrolidone permit dispersion of said tocopheryl retinoate over the entire ulcerated lesion to be treated with said tocopheryl retinoate, and the tocopheryl retinoate remains in contact with lesion for a prolonged period of time. Thus, the tocopheryl retinoate is permitted to work directly on said lesion for said prolonged period of time.

In a preferred embodiment, the composition includes an effective amount of antioxidant, which preferably is ascorbic acid, derivatives of ascorbic acid or tocopherol.

In a third aspect of the invention, there is provided a method of topically treating the ulcerated lesion of the gastrointestinal tract. The method comprises orally administering tocopheryl retinoate in a form in which said tocopheryl retinoate is adsorbed on a carrier which is capable of being retained in said lesion for a prolonged period of time, whereby the beneficial effects of said tocopheryl retinoate are topically available to said lesion for said prolonged period of time.

In a preferred embodiment, said tocopheryl retinoate is administered together with hydroxypropylcellulose and polyvinylpyrrolidone.

The tocopheryl retinoate is a highly viscous and resinous substance. It is orally administrable so as to effectively demonstrate its remarkable curative effects in the treatment of peptic ulcer.

Thus, an object of the present invention is to provide an anti-peptic ulcer agent comprising (a) a powdery material which includes tocopheryl retinoate, light silicic anhydride, and an antioxidant; (b) a low substituted hydroxypropylcellulose; and (c) polyvinylpyrrolidone.

The anti-peptic ulcer agent contains tocopheryl retinoate as an active ingredient. It is preferably included in an amount ranging from approximately 0.05% to 60.0% by weight on the basis of a total weight of the preparations. The agent may also comprise at least one compounded selected from ascorbic acid, a derivative of ascorbic acid, and tocopherol as an antioxidant.

Accordingly, the present invention provides for an anti-peptic ulcer agent which preferably comprises the following specific formulation:

| (a) powdery material comprising: | |
| --- | --- |
| tocopheryl retinoate | 0.05–60.0% by weight |
| light silicic anhydride | 0.05–50.0% by weight |

| -continued | |
|---|---|
| antioxidant selected form ascorbic acid, its derivative, or tocopherol | as required |
| (b) low substituted hydroxypropyl-cellulose | 5.0-20.0% by weight |
| (c) polyvinylpyrrolidone | 2.0-15.0% by weight |

An excipient and/or a lubricant may also be provided in the anti-peptic ulcer agent of the present invention. The excipient may be at least one compound selected from corn starch, fine crystalline cellulose, lactose, saccharose, and hydroxypropyl starch. The lubricant may be at least one compound selected from magnesium stearate, talc, light silicic anhydride or hardened plant oil. Accordingly, the present invention provides for an anti-peptic ulcer agent which preferably comprises the following specific formulation:

| (a) powdery material comprising: | |
|---|---|
| tocopheryl retinoate | 5-40% by weight |
| light silicic anhydride | 5-40% by weight |
| antioxidant selected form ascorbic acid, its derivative, or tocopherol | as required |
| (b) low substituted hydroxypropyl-cellulose | 8-15% by weight |
| (c) polyvinylpyrrolidone | 3-9% by weight |
| (d) corn starch | 5-60% by weight |
| (e) magnesium stearate | 1-4% by weight (with respect to a total weight of the preparations) |

Preferably, the anti-peptic ulcer agent according to the present invention may have specific formulations as follows (in which the weight is based on a total weight of the preparations):

| tocopheryl retinoate | 5-40% by weight, more preferably 15-30% by weight |
|---|---|
| light silicic anhydride | 5-40% by weight, more preferably 25-35% by weight |
| ascorbic acid or tocopherol | 0.05-0.4% by weight, more preferably 0.15-0.3% by weight |
| hydroxylpropylcellulose of a low substitution degree | 8-15% by weight, more preferably 10-13% by weight |
| polyvinylpyrrolidone | 3-9% by weight, more preferably 3-5% by weight |
| corn starch | 5-60% by weight, more preferably 10-14% by weight |
| magnesium stearate | 1-4% by weight, more preferably 2-4% by weight |

DETAILED DESCRIPTION OF THE PREFERRED EMBODIMENTS

Figure 1:
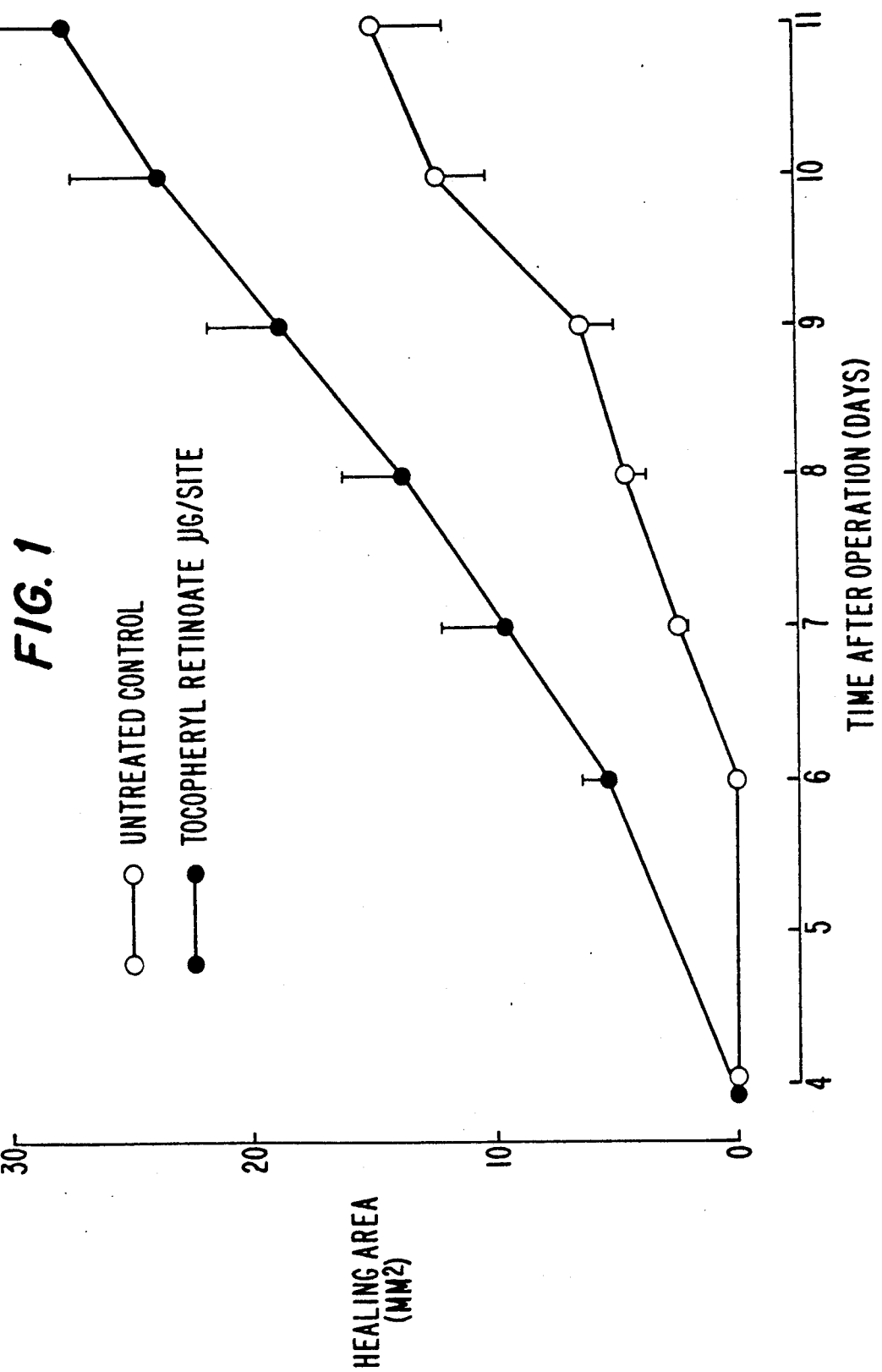
FIG. 1 shows the effects in promoting tissue growth.

In accordance with the invention, tocopheryl retinoate exhibits an extremely potent activity in promoting granulation and mucosa formation. That is, when tocopheryl retinoate contacts the ulcerated lesions of the digestive tract, this active ingredient works to expedite the formation of muscle layer of said lesions, and to promote the formation of thick mucosal layer for protecting from gastric acid for a prolonged period of time.

More particularly, it has been found that tocopheryl retinoate has an effect upon proliferation of fibroblasts functioning in tissue formation, promotion of production of connective tissue substrates such as collagen, glycosaminoglycan and the like from fibroblasts, and promotion of angiogenesis of peripheral blood vessels in the submucosal layer. It is also contemplated that tocopheryl retinoate could function as a potent anti-peptic ulcer agent even when used in an extremely smaller dosage than anti-peptic ulcer agents currently on the market, if the tocopheryl retinoate could be selectively dispersed to act upon ulcerated lesions on the inner wall of the digestive tract.

It has been found that oral preparations of tocopheryl retinoate prepared in a conventional manner (i.e., by adsorption with silicic anhydride or the like) cannot exhibit the potent anti-peptic ulcer activity inherent in tocopheryl retinoate. Since tocopheryl retinoate acts directly on ulcer lesions, it is desirable that the compound adhere to a wide area of ulcer legions in order to sufficiently exhibit its potent tissue formation activity. It is to be noted, however, that the tocopheryl retinoate is poorly dispersed when adsorbed and powdered. Additionally, in conventional powdered preparations, powders of tocopheryl retinoate aggregate with each other, due to their own physical characteristics, prior to dispersion into fine powders in the digestive tract. As a result, the tocopheryl retinoate suffers from the disadvantage that it cannot exhibit its curative effect on ulcerated lesions.

It has also been noted that, although tocopheryl retinoate possesses a potent tissue formation activity, the reason tocopheryl retinoate fails to exhibit its anti-peptic ulcer effect is based on a low degree of dispersibility and adhesion to ulcerated lesions of conventional preparations containing tocopheryl retinoate. An extensive review has been made to solve these problems and to investigate types of preparations that are capable of exhibiting the excellent anti-peptic ulcer effects that are inherent in tocopheryl retinoate. As a result, it has been found that tocopheryl retinoate in a semi-solid and resinous nature can be powdered with the aid of light silicic anhydride and prepared into formulations by admixing at least hydroxypropylcellulose of a low degree of substitution and polyvinylpyrrolidone with the powdery material. Oral preparations with such unique formulations can be dispersed to a sufficient degree in the digestive tract and selectively adhered onto ulcerated lesions. The present invention is discussed on the basis of the findings.

The present invention, particularly formulations for preparations comprising a powdery material comprising tocopheryl retinoate, light silicic anhydride and an anti-oxidant, a low substituted hydroxypropylcellulose, and polyviniylpyrrolidone, is characterized in that it ensures a sufficient dispersibility of the preparations in the digestive tract and a satisfactory adhesion of the tocopheryl retinoate on ulcerated lesions. Thus, the invention exhibits an anti-ulcer activity on the basis of the tissue formation activity inherent in tocopheryl retinoate.

Anti-peptic ulcer agents currently on the market can be classified into two types, one type inhibiting or relaxing an offensive factor and the other increasing a defensive factor. Anti-peptic ulcer agents of the type inhibiting the offensive factor, such as $H_2$ receptor antagonists, proton pump inhibitors, muscarin receptor antagonists and the like, inhibit secretion of substance such as gastric acid, pepsin and the like which cause ulcer formation. These offensive factor agents induce ulcerated lesions to be healed naturally by the inherent ability of the body to form tissue reparation. This method of healing is referred to as indirect therapy. These particular agents, however, are insufficient to aid in formation of mucosal tissues. Such a deficiency often leads to a relapse and the worsening of ulcer as a rebound phenomenon after the administration of the agent has been discontinued. These characteristics are being recognized with considerably higher frequency. Thus, risk factors are often a major problem of anti-peptic ulcer agents of the type inhibiting the offensive factor.

Alternatively, there are anti-peptic ulcer agents of the type increasing the defensive factor which induce secretion of mucus, strengthen protection of ulcerated lesions, and which form tissue reparation. These agents, however, cannot be said to be sufficient in both action and effect.

In contrast, the anti-peptic ulcer agent according to the present invention contains tocopheryl retinoate as an active ingredient. It differs from conventional anti-ulcer agents and is an agent for direct therapy in promoting an increase in a substrate level at ulcerated lesions. It is capable of acting upon fibroblasts that function in the formation of tissues, promoting production of acid mucopolysaccharide or the like. Such as collagen or glycosaminoglycan from fibroblasts, and forming ulcerated mucosal tissues by promoting angiogenesis of peripheral circulation of submucosa. Thus, balancing of tissue formation as a whole is achieved.

In accordance with the present invention, the formation of preparations containing tocopheryl retinoate having the above activities can exhibit the effects inherent in tocopheryl retinoate by ensuring an adherability to ulcerated lesions.

The anti-peptic ulcer agents according to the present invention are based upon unique formulations for preparations. They are characterized by a powdery formulation prepared by adsorbing tocopheryl retinoate in a semi-solid and highly viscous nature which acts as an active ingredient onto light silicic anhydride which acts as an adsorbent, together with an antioxidant. The agents are formulated with low subsituted hydroxypropylcellulose and polyvinylpyrrolidone as essential ingredients.

The anti-peptic ulcer agents according to the present invention may be prepared into pharmaceutically acceptable forms such as tablets, powders, granules, capsules and the like. Optionally, additives such as an excipient, lubricant or the like may be included which contribute to the effective fomulation of the curing agents.

In the anti-peptic ulcer agents according to the present invention, tocopheryl retinoate should be dispersed in the digestive tract in finely and uniformly divided form so that it should be in a powdery state. The powdery state of tocopheryl retinoate is advantageous from the viewpoint of pharmaceutical technology in that various forms suitable for oral administration may be selected from. Such compounds as low substituted hydroxypropylcellulose and polyvinylpyrrolidone serve to promote dispersion of the powdery material. These compounds rapidly disperse the powdery material which can favorably adhere to the ulcerated lesion sites and eventually demonstrate the pharmacological activity of tocopheryl retinoate.

Accordingly, the anti-peptic ulcer agents according to the present invention are disigned to demonstrate potent tissue formation activity inherent in tocopheryl retinoate in association with the other essential ingredients, thus exhibiting its remarkable anti-peptic ulcer effect as will be described in detail hereinbelow.

The present invention provides for anti-peptic ulcer agents having a formulation comprising at least (a) powdery material consisting of tocopheryl retinoate, light silicic anhydride and an antioxidant: (b) low subsituted hydroxypropylcellulose; and (c) polyvinylpyrrolidone.

The following is an individual description of each of the ingredients. (a) Powdery material:

For the anti-peptic ulcer agents according to the present invention, tocopheryl retinoate of a highly viscous and resinous material should first be powdered.

The technique of pulverizing a highly viscous agent adsorbed on an adsorbent such as silicic acid or the like is disclosed, for example, in Japanese Patent Publication (Kokoku) No. 46,899/1974. A technique similar to this may be applied to the pulverizing of tocopheryl retinoate to be used as an active ingredient for the present invention. It is noted, however, that the present invention particularly uses light silicic anhydride as an adsorbent. The reason for use of light silicic anhydride is that it has a fine particle size, up to about 3.0 microns preferably having an average diameter ranging from about 1.0 to 2.0 microns, and a large surface area. Thus, tocopheryl retinoate is favorably adsorbed. Additionally, its uniformity and flowability are so high that good dispersibility in the digestive tract is ensured. It is to be understood that tocopheryl retinoate is readily oxidized by pulverizing with light silicic anhydride so that it is preferably required to use an antioxidant in order to enhance the stability of the tocopheryl retinoate. Although various antioxidants may be used, it is preferred to use ascorbic acid, a derivative of ascorbic acid or tocopherol. As derivatives of ascorbic acid, a pharmaceutically acceptable salt or ester may be used.

The powdery material comprising tocopheryl retinoate, light silicic anhydride and the antioxidant may be prepared by the following procedures.

Tocopheryl retinoate and antioxidant are dissolved in a pharmaceutically acceptable and conventionally usable organic solvent such as ethanol, acetone, or n-hexane. Light silicic anhydride is then uniformly suspended in the resulting solution. After the solvent is distilled off, a powdery material remains in which tocopheryl retinoate is present in a stable state. After optical addition of a lubricant, an antistatic agent or other additive, the powdery material may then be pulverized to form a more finely divided material.

The amount of tocopheryl retinoate to be formulated as an active ingredient in the present invention may vary in a wide range according to condition of disease. Accordingly, the amount of tocopheryl retinoate is not limited to a particular range. This leads to putting no restriction upon the amount of light silicic anhydride to be used as the adsorbent with respect to the amount of tocopheryl retinoate. It is to be noted that the viscosity of the powdery material should not be allowed to become too high because it is uniformly mixed with low substituted hydroxypropyl cellulose and polyvinylpyrrolidone in a subsequent step. From the above point of view, it is preferred that the amounts of the tocopheryl retinoate and the light silicic anhydride each range from 0.5% to 50% by weight on the basis of total weight of the formulation. The antioxidant may be in an appropriate amount as pharmaceutically acceptable for use as a stabilizer. However, the preferred range is from 0.5% to 2.0% by weight on the basis of the weight of tocopheryl retinoate.

(b) Low substituted hydroxypropyl cellulose and (c) Polyvinylpyrrolidone:

In order to rapidly disperse the powdery material of group (a) in the digestive tract and to consequently allow the tocopheryl retinoate to specifically adhere to ulcerated lesion sites, the low substituted hydroxypropylcellulose and polyvinylpyrrolidone should be formulated along with the powdery material. It is preferred that the low substituted hydroxypropylcellulose is the low subsituted hydroxypropyl ether of cellulose containing not less than 5.0% hydroxypropoxy ($-OC_3H_6-OH$) groups and not more than 16.0 percent of hydroxypropyl groups, calculated on the dried basis, and polyvinylpyrrolidone has a molecular weight of about 30,000 to 40,000, in this invention. Amounts of these two ingredients are not critical and may preferable range from approximately 10% to 80% by weight for the low substituted hydroxylpropylcellulose and from approximately 3% to 30% by weight for the polyvinylpyrrolidone, each on the basis of a total weight of the therapeutic formulation.

As described above, the powdery formulation of the present invention includes low substituted hydroxypropylcellulose and polyvinylpyrrolidone as essential ingredients for the anti-peptic ulcer agent. The formulation may be prepared by adding to the powdery material of group (a) both the low subsituted hydroxypropylcellulose and the polyvinylpyrrolidone and mixing the resultant mixture in a uniform manner.

As described above, the powdery formulation may be used intact as an objective anti-peptic ulcer agent. Thus the anti-peptic ulcer agent according to the present invention preferably comprises:

| (a) powdery material comprising: | |
| --- | --- |
| tocopheryl retinoate | 0.05–60.0% by weight |
| light silicic anhydride | 0.05–50.0% by weight |
| antioxidant selected from ascorbic acid, its derivative, or tocopherol | as required |
| (b) low substituted hydroxypropylcellulose | 5.0–20.0% by weight |
| (c) polyvinylpyrrolidone | 2.0–15.0% by weight |

There may be added to the powdery formulation various pharmaceutically acceptable additives. Such additives may include, for example, excipients, disintegrating agents, connecting agents, lubricants, preservatives, stabilizers, colorants, corrigents, flavoring agents, dissolution accessories, suspending agents, flowing agents, buffers, pH adjusting agents and the like.

The excipients may be any pharmaceutically acceptable and may include, for example, corn starch, fine crystalline cellulose, lactose, white sugar, glucose, sucrose, hydroxypropyl starch, or sodium chloride. Among the excipients, at least one may be selected from the group consisting of corn starch, finely crystalline cellulose, lactose, sucrose, and hydroxypropyl starch, with corn starch being more preferable. The amount of excipient to be used is not critical and may be as large as conventionally used.

The disintegrating agents may include, for example, carboxymethyl cellulose calsium, cross-linkable carboxymethyl cellulose, cross-linkable carboxymethyl cellulose sodium, hydroxypropylcellulose of a low substitution degree, polyvinylpyrrolidone, sodium starch glycolate, partially α-converted starch, or processed starch. The amount of disintegrating agent to be used is also not critical and may not be needed if the anti-ulcer agent is capable of being rapidly disintegrated.

The connecting agents may include, for example, acacia powders, gum arabic, gelatin, tragacanth, hydroxypropylcellulose, hydroxypropyl methylcellulose, partially α-converted starch, or polyvinylpyrrolidone. The amount of connecting agents to be used is not critical and may be in such an amount as conventionally used.

The lubricants may be any conventional type that is usable and pharmaceutically acceptable. They may include, for example, magnesium stearate, talc, silicic anhydride, hardened plant oil and the like. Magnesium stearate is preferred. The amount of lubricant is not critical and may be as large as conventionally used.

The dissolution accessories may include, for example, polyethylene glycol, sorbitan monooleate, polyoxyethylene hardened castor oil, sodium laurylsulfate and the like.

The anti-peptic ulcer agents according to the present invention may contain an appropriate amount or amounts of the above additive or additives in addition to the powdery formulation. In a preferred embodiment, there may be added to the powdery formulation, for example, corn starch as an excipient and magnesium stearate as a lubricant. More specifically, the formulation may contain the following ingredients on the basis of a total weight of the therapeutic preparations:

| | |
| --- | --- |
| tocopheryl retinoate | 5–40% by weight, preferably 15–30% by weight |
| light silicic anhydride | 5–40% by weight, preferably 25–35% by weight |
| ascorbic acid or tocopherol | 0.05–0.4% by weight, preferably 0.15–0.3% by weight |
| hydroxylpropylcellulose of low substitution degree | 8–15% by weight, preferably 10–13% by weight |
| polyvinylpyrrolidone | 3–9% by weight, preferably 3–5% by weight |
| corn starch | 5–60% by weight, preferably 10–40% by weight |
| magnesium stearate | 1–4% by weight, preferably 2–4% by weight |

Although the anti-peptic ulcer agents according to the present invention may be prepared in a conventional pharmaceutical manner, they may be prepared by the following procedures:

To the powdery material of group (a) are added hydroxypropylcellulose of a low substitution degree, polyvinylpyrrolidone and a portion of the excipient. The mixture is subjected to dry granulation after uniform admixture and pulverized to powdery formations. Alternatively, the hydroxypropylcellulose and a portion of the excipient are added to the powdery material. The resultant mixture is admixed to give a uniform mixture which is then mixed with ethanol and subjected to wet granulation. The wet granules are then dried and pulverized. To the pulverized material are added the remainder of the excipient and the lubricant which is then mixed in a uniform manner.

The powdery formulation of present invention, or the formulation to which the additive(s) is(are) added, may be formulated as conventional preparations. These preparations include powders, fine granules, granules, capsules or tablets. The tablets may be coated if necessary.

As described above, the anti-peptic ulcer agents may be prepared by formulating the powdery material comprising group (a), low substituted hydrooxypropylcellulose, and polyvinylpyrrolidone. One or more additives may be included as desired. The anti-peptic ulcer agents according to the present invention are designed to be readily dispersed in the digestive tract when orally administered and to allow tocopheryl retinoate to be selectively adsorbed onto ulcerated lesions on the inner wall of the digestive tract for a prolonged period of time, that is, for about 6 hrs. Thus, the potent tissue growth activity inherent in tocopheryl retinoate is exhibited.

The markable effects provided by the present invention are confirmed by the following biological activity tests.

In administering the anti-peptic ulcer agent according to the present invention to patients, dosage and number of administrations are affected by age and sex of patients, depth of ulcerated lesions sites, a medical doctor's judgement and the like. However, it is generally preferred to administer the anti-peptic ulcer agent to a patient weighing 60 kilograms from once to three times daily so as to apply tocopheryl retinoate in a range from 0.05% to 60.0% by weight, preferably from 15% to 40% by weight, per single dose.

The present invention will be described more in detail by way of examples and biological activity tests.

EXAMPLE 1

Capsules (175 mg per capsule)

| | |
|---|---|
| Tocopheryl retinoate | 50.0 grams |
| Light silicic anhydride (Syloid-266 ®) | 55.0 grams |
| Ascorbic acid | 0.5 grams |
| Low substituted hydroxypropylcellulose | 20.0 grams |
| Corn starch | 36.5 grams |
| Polyvinylpyrrolidone (PVP.K-30 ® average molecular weight about 40,000) | 7.0 grams |
| Magnesium stearate | 6.0 grams |
| Total | 175.0 grams |

The capsules were prepared as follows:

Tocopheryl retinoate (50.0 grams) was dissovled in 500 ml of acetone, and 50 ml of an ethanolic solution of 0.5 grams of ascorbic acid and 55.0 grams of light silicic anhydride (Syloid-266 ®) were added to the solution. After the mixture was stirred, the solvent was evaporated. The residue left was then pulverized to finely divided material to which 20.0 grams of low substituted hydroxypropylcellulose, 15.0 grams of corn starch and 7.0 grams of polyvinylpyrrolidone (PVP K-30 ®) were added. After admixture, the resultant uniform mixture was then dry-granulated and pulverized. To the pulverized material were added 21.5 grams of corn starch and 6.0 grams of magnesium stearate, and the resultant powdery formulation was filled in capsules each in the amount of 175 mg.

EXAMPLE 2

Capsules (175 mg per capsule)

| | |
|---|---|
| Tocopheryl retinoate | 50.0 grams |
| Light silicic anhydride (Syloid-266 ®) | 55.0 grams |
| Tocopherol | 0.5 grams |
| Low substituted hydroxypropylcellulose | 20.0 grams |
| Corn starch | 36.5 grams |
| Polyvinylpyrrolidone (PVP.K-30 ® average molecular weight about 40,000) | 7.0 grams |
| Magnesium stearate | 6.0 grams |
| Total | 175.0 grams |

The capsules were prepared in substantially the same manner as in Example 1 (tocopherol was used instead of ascorbic acid), and the powdery formulation prepared was then filled in the capsules each in the amount of 175 mg.

EXAMPLE 3

Capsules (175 mg per capsule)

| | |
|---|---|
| Tocopheryl retinoate | 25.0 grams |
| Light silicic anhydride (Syloid-266 ®) | 27.5 grams |
| Ascorbic acid | 0.25 grams |
| Low substituted hydroxypropylcellulose | 20.0 grams |
| Corn starch | 84.75 grams |
| Crystalline cellulose (Avicel ®) | 7.0 grams |
| Polyvinylpyrrolidone (PVP.K-30 ®) | 7.0 grams |
| Magnesium stearate | 3.5 grams |
| Total | 175.0 grams |

The capsules were prepared as follows:

Tocopheryl retinoate (25.00 grams) was dissovled in 250 ml of acetone, and 25 ml of an ethanolic solution of 0.25 grams of ascorbic acid and 27.50 grams of light silicic anhydride (Syloid-266 ®) were added to the solution. After the mixture was stirred, the solvent was evaporated. The residue left was then pulverized to finely divided material to which 20.0 grams of low substituted hydroxypropylcellulose, 15.0 grams of corn starch, 7.00 grams of crystalline cellulone (Avicel ®) and 7.00 grams of polyvinylpyrrolidone(PVP.K-30 ®) were added. After admixture, the resultant uniform mixture was then dry-granulated and pulverized. To the pulverized material were added 69.75 grams of corn starch and 3.50 grams of magnesium stearate, and the resultant powdery formulation was filled in capsules each in the amount of 175 mg.

EXAMPLE 4

Capsules (65 mg per capsule)

| | |
|---|---|
| Tocopheryl retinoate | 5.00 grams |
| Light silicic anhydride (Syloid-266 ®) | 5.50 grams |
| Ascorbic acid | 0.05 grams |
| Low substituted hydroxypropylcellulose | 8.00 grams |
| Corn starch | 30.45 grams |
| Crystalline cellulose (Avicel ®) | 10.00 grams |
| Polyvinylpyrrolidone (PVP.K-30 ®) | 5.00 grams |
| Magnesium stearate | 1.00 grams |
| Total | 65.0 grams |

The capsules were prepared in substantially the same manner as in Example 3, and the powdery formulation prepared was then filled in the capsules each in the amount of 65 mg.

EXAMPLE 5

Capsules (175 mg per capsule)

The powdery formulation having the same ingredients as in Example 3 were prepared as follows:

Tocopheryl retinoate (25.00 grams) was dissovled in 250 ml of acetone, and 25 ml of an ethanolic solution of 0.25 grams of ascorbic acid and 27.50 grams of light silicic anhydride (Syloid-266®) were added to the solution. After the mixture was stirred, the solvent was evaporated. The residue left was then pulverized to finely divided material to which 20.0 grams of low substituted hydroxypropylcellulose, 15.0 grams of corn starch, and 7.00 grams of crystalline cellulone (Avicel®) were added. After admixture, the resultant uniform mixture was then mixed with 50 ml of an ethanolic solution of 7.00 grams of polyvinylpyrrolidone (PVP.K-30®) and granulated. After pulverization, 69.75 grams of corn starch and 3.50 grams of magnesium stearate were added and mixed, and the resultant powdery formulation was filled in capsules each in the amount of 175 mg.

EXAMPLE 6

Tablets (175 mg per tablet)

The powdery formulation having the same ingredients as in Example 1 was tabletted in the amount of 175 mg to give tablets having the diameter of 8 mm.

EXAMPLE 7

Fine granules

| Tocopheryl retinoate | | 0.100 grams |
|---|---|---|
| Light silicic anhydride (Syloid-266 ®) | | 0.110 grams |
| Ascorbic acid | | 0.001 grams |
| Low substituted hydroxypropylcellulose | | 12.000 grams |
| Corn starch | | 63.289 grams |
| Crystalline cellulose (Avicel ®) | | 20.00 grams |
| Polyvinyl pyrrolidone (PVP.K-30 ®) | | 4.000 grams |
| Magnesium stearate | | 0.500 grams |
| | Total | 100.000 grams |

The powdery formulation was prepared in substantially the same manner as in Example 3, and the resultant powdery formulation was filtered using 32 mesh and 80 mesh filters yielding fine granules.

EXAMPLE 8

Granules

| Tocopheryl retinoate | | 2.00 grams |
|---|---|---|
| Light silicic anhydride (Syloid-266 ®) | | 2.20 grams |
| Ascorbic acid | | 0.02 grams |
| Low substituted hydroxypropyl cellulose | | 12.00 grams |
| Corn starch | | 59.08 grams |
| Crystalline cellulose (Avicel ®) | | 20.00 grams |
| Polyvinyl pyrrolidone (PVP.K-30 ®) | | 4.00 grams |
| Magnesium stearate | | 0.70 grams |
| | Total | 100.00 grams |

The granules were prepared in substantially the same manner as in Example 3.

Tests for Biological Activities:

The anti-peptic ulcer agents according to the present invention will be tested for their anti-peptic ulcer and tissue growth activities in accordance with following procedures.

I. Tissue Growth Activities:

1. Effect on Promotion of Tissue Growth

The effect of tocopheryl retinoate upon promotion of tissue growth is reviewed according to the rabbit ear chamber (hereinafter referred to as REC) method.

Methods:

An ethereal solution of tocopheryl retinoate was dropped on a round table at a central portion of REC and dried. Separately, a hole with a diameter of 5 mm was punched-out at the auricula of the rabbit, and the above REC was attached to the hole of the auricula in conventional manner. Observations have been made for enlargement of tissue growth area at the lesion site until day 11 after operation. The tocopheryl retinoate was adjusted so as to amount to 100 µg per punched-out site, and a group of 2 rabbits used for tests was compared with a control group to which no tocopheryl retinoate was applied. The tissue growth area is represented in a mean value.

Results:

For a group of treatment, tissue growth has been recognized from day 4 after operation, while it has been recognized from day 6 thereafter for a control group. The results demonstrating periodical changes are shown in FIG. 1.

As apparent from the results shown in FIG. 1, the tissue reparation is recognized to a remarkable extent by a group to which tocopheryl retinoate was applied, as compared with a group to which no tocopheryl retinoate was applied. It is thus found that the tocopheryl retinoate has a potent tissue reparation activity.

2. Effect on Promotion of Granulation Formation:

The effect of tocopheryl retinoate upon promotion of the granulation formulation is reviewed by using the cotton pellet-induced granulation method.

Methods:

Cotton pellets were immersed in an alcoholic solution of tocopheryl retinoate and implanted subcutaneously at the back of a rat in a conventional manner after the alcohol had been evaporated off. Granulation tissues which adhered to the cotton pellets were quantitated after removal on day 8 after operation.

The tocopheryl retinoate was adjusted to 0.125 mg, 0.5 mg, 2.0 mg, and 8.0 mg, per pellet. A treatment group was compared with a vehicle group in which only alcohol was infiltrated into cotton pellets and the pellets were implanted subcutaneously after the alcohol had been evaporated and dried.

Figure 2:
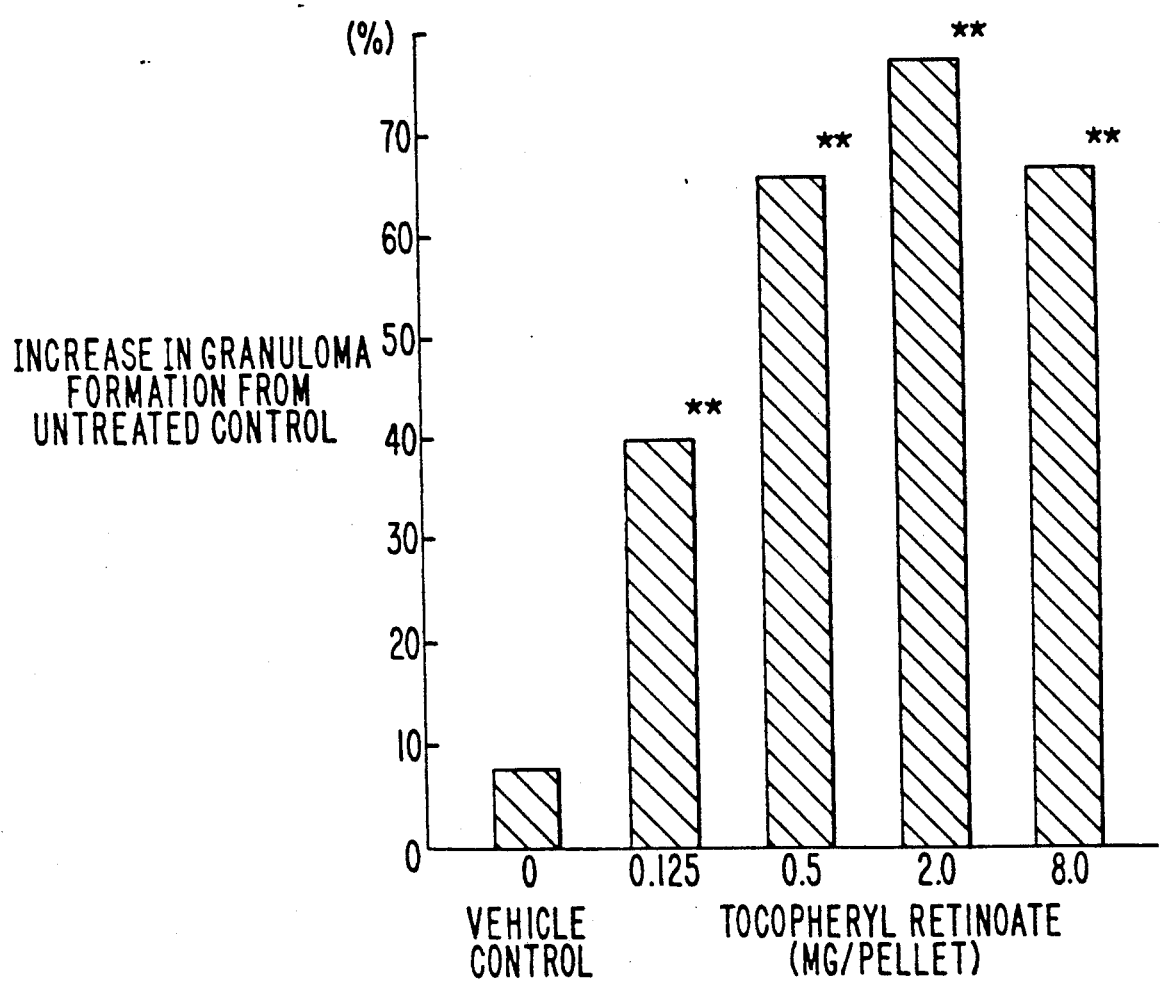
FIG. 2 shows effects in promoting granulation formulation.

Results:

By using granulation tissues formed in the vehicle group as a control, the degree of formation of granulation tissues in the treatment group was indicated by percentage. The results are shown in FIG. 2.

From the results, it is recognized that granulation tissues have been significantly increased in the group of treatment in which tocopheryl retinoate was applied.

3. Effect on Increase in Fibroblasts:

By using fibroblasts of rats obtained by the cotton pellet-induced granulation method, the effect of tocopheryl retinoate on an increase in the fibroblasts has been reviewed on the basis of an uptake of thymidine into the cells and a number of cells increased.

Methods

Fibroblasts were obtained from rats in accordance with the cotton pellet-induced granulation method. The fibroblasts were inoculated in the amount of $4 \times 10^4$ cells per dish on DME media and a 0.005% acetone solution of tocopheryl retinoate was added thereto in concentrations of $10^{-10}$ mole, $10^{-9}$ mole, and $10^{-8}$ mole, respectively. The media were incubated for 5 days and fibroblasts were counted on day 5 after incubation.

Separately, the fibroblasts were inoculated on DME media in the amount of $2 \times 10^5$ cells per dish to which a 0.005% acetone solution of tocopheryl retinoate was added in concentrations of $10^{-10}$ mole, $10^{-9}$ mole and $10^{-8}$ mole, respectively. After incubation for 4 days, $^3H$ labelled thymidine was added on day 4 in the amount of 0.5 μ Ci/dish. Cells were gathered in 5 hours, and radioactivity was measured using a liquid scintillation counter.

As control groups, a vehicle group containing a 0.005% acetone solution and a control group containing no acetone vehicle was used.

Results:
The results are shown in Table 1.

proline as an indicator by means of the method of Kivirikko, K. I., et al., and the amount of glycosaminoglycan was quantitated using uronic acid as an indicator by means of the method of Bitter, Tand Muir, and H. M.

The same procedures were applied to a vehicle group in which only ethanol was infiltrated. Cotton pellets were implanted subcutaneously after evaporation and drying. The vehicle group was used a control.

Results:

TABLE 1

| Groups | Amount of Addition[1] | Number of Media | Amount of Intake of Thymidine[2] | Number of Media | Number of Cells[3] |
|---|---|---|---|---|---|
| No addition | — | 3 | 12845 ± 1871 | NT | NT |
| Vehicle | 0 | 4 | 14033 ± 1053 (100) | 3 | 1.13 ± 0.03 (100) |
| Tocopheryl retinoate | $10^{-10}$ | 4 | 15432 ± 444** (117) | NT | NT |
| Tocopheryl retinoate | $10^{-9}$ | 4 | 16892 ± 507** (120) | 3 | 1.48 ± 0.08 (131) |
| Tocopheryl retinoate | $10^{-8}$ | 4 | -18059 ± 397*** (129) | 3 | 1.48 ± 0.22 (131) |

Notes:
[1] Molar concentration
[2] dpm/flask
[3] $10^5$ cells/disk
, *: with significant difference (margin of errors: $p < 0.01$, $p < 0.001$, resp.)
NT: not tested As shown in FIG. 1, it was found that the amounts of uptake of thymidine and numbers of the cells were obviously increased in the treatment group in which tocopheryl retinoate was applied. Moreover, the treatment group demonstrats the effect on the promotion of an increase in fibroblasts having a significant difference relative to the vehicle group.

4. Effects on promotion of production of collagen and glycosaminoglycan:

The effects of tocopheryl retinoate on promotion of the production of collagen and glycosaminoglycan were reviewed by using granulation tissues obtained by means of the cotton pellet-induced granulation method.

Methods:

Cotton pellets were immersed in an ethanol solution of tocopheryl retinoate so as to contain 2.0 mg of tocopheryl retinoate. The ethanol was removed by evaporation. The cotton pellets were then implanted subcutaneously at the back of a rat in a conventional manner. The cotton pellets were removed on days 4, 7, and 10 after operation. The amount of collagen contained in the granulation tissues were quantitated using hydroxyproline as an indicator by means of the method of Kivirikko, K. I., et al., and the amount of glycosaminoglycan was quantitated using uronic acid as an indicator by means of the method of Bitter, Tand Muir, and H. M.

The results are shown in Table 2.

TABLE 2

| Day of Measurement | Number of Rats | Collagen[1] Mean value ± Deviation | Glycosaminoglycan[2] Mean value ± Deviation |
|---|---|---|---|
| Day 4 | | | |
| Group V[3] | 8 | 451.46 ± 153.17 (100) | 17.52 ± 8.30 (100) |
| Group T[4] | 10 | 886.37 ± 381.08** (196) | 28.79 ± 6.35** (164) |
| Day 7 | | | |
| Group V | 8 | 698.09 ± 263.5 (100) | 16.59 ± 4.43 (100) |
| Group T | 10 | 1295.83 ± 480.53** (186) | 29.34 ± 9.44** (177) |
| Day 8 | | | |
| Group V | 8 | 313.59 ± 232.52 (100) | 4.24 ± 2.79 (100) |
| Group T | 10 | 1301.07 ± 443.90*** (415) | 18.49 ± 3.39*** (436) |

Notes:
[1] μg/sample: indicated as an amount of hydroxyproline
[2] μg/sample: indicated as an amount of uronic acid
[3] vehicle group
[4] tocopheryl retinoate group
, *: with significant difference It is apparent from the results shown in Table 2, that the tocopheryl retinoate groups have indicate that the effects on the promotion of the production of both collagen and glycosaminoglycan at each day of measurement showed a significant difference compared to the vehicle group.

5. Effect on promotion of angiogenesis:

The effect of tocopheryl retinoate on promotion of the angiogenesis for the granulation tissues obtained by means of the cotton pellet-induced granulation method was reviewed by endoscopic observations and the carmine pigment injection method, in which the pigment is not transferable through tissues.

Methods:

Cotton pellets were immersed in an ethanol solution of tocopheryl retinoate so as to contain 2.0 mg of tocopheryl retinoate and ethanol was removed by evaporation. The cotton pellets were then implanted subcutaneously on the back of a rat in conventional manner.

To tail veins of a rat were administered a 10% carmine solution containing 5% gelatin at the rate of 70 ml/kg on day 7 after operation. The rat was allowed to stay for several hours in a cold chamber at temperatures below 4° C. The surrounding skin, cotton pellet, and granulation tissues were removed. They were subjected to formalin fixation and paraffin embedding in a conventional manner. Thereafter, the tissues were sliced, subjected to the H.E. stain, and observed microscopically The carmine pigment in the separately isolated cotton pellet was quantitated according to a method equivalent to Kimura et al.

As a control a vehicle group, in which only ethanol was immersed and cotton pellets were implanted subcutaneously after evaporation and drying, was reviewed and compared in substantially the same manner.

Results:

The microscopy has apparently revealed promotion of the angiogenesis of the tocopheryl retinoate group compared with the vehicle group.

More than 60% of penetrating blood vessels to cotton pellets have been recognized at deep portions for the tocopheryl retinoate group. And a penetration to the deepest portion has also been recognized.

The carmine pigment quantitation has revealed promotion of angiogenesis in the tocopheryl retinoate group with a more significant difference than in the vehicle group.

The results are shown in Table 3.

TABLE 3

| Agent Applied | Number of Samples | Amounts of Carmine Pigment[1] |
|---|---|---|
| Vehicle | 8 | 1.50 ± 1.17 |
| Tocopheryl retinoate | 9 | 3.11 ± 0.815* |

Notes:
[1] mg granuloma
*: with significant difference (margin of error: p <0.01)

As apparent from the results of Tests 1 to 5, it has been found that tocopheryl retinoate exhibits tissue growth activities by increasing fibroblasts supporting the tissue growing step, promoting the production of connective tissue substrates such as collagen, glycosaminoglycan and so on from the fibroblasts, and promoting the antiogenesis of peripheral blood vessels.

This reveals that tocopheryl retinoate demonstrates an effective and remarkable tissue growth activity when locally administered directly to lesion sites.

Therefore, the anti-peptic ulcer agents according to the present invention on the basis of a specific unique formulation allowing tocopheryl retinoate to act selectively upon lesion sites on the mucosa in the digestive tract can significantly promote the tissue growth on lesion sites, thus exhibiting a remarkable anti-peptic ulcer effect.

II. Effects for Treatment of Peptic Ulcer:

The effects for treatment of peptic ulcer were by reviewed using rat's acetic acid ulcer models.

For each test, the rat's acetic acid ulcer models were prepared and the healing effects are judged by following procedures:

1. Method for Preparation of Rat's Acetic Acid Ulcer Models:

Gastric ulcer was formed in rats according to the Takagi et al.'s method (Japan. J. Pharmacol.: 18, 9, 1968). Rats of the SD strain were anesthetized and subjected to an abdominal operation for injection of 0.05 ml of 15% acetic acid underneath the serosa of the stomach. Each sample was orally administered twice daily until day 13 from day 1 after day 0 (day of operation). The stomach was sectioned again on day 14 and ulcer lesions on the inner wall of the stomach were observed. The curing effect was evaluated as an ulcer index by indicating a size of an ulcer lesion (long diameter x short diameter) and as an improvement rate by comparison with a group of non-administration (administration of a vehicle only).

2. Effect on Treatment of Ulcer (Part 1):

A suspension of each amount of tocopheryl retinoate as shown in Table 1 was suspended in 1.0% (w/v) of polyoxyethylenehardened castor oil (HCO-60) was used for testing its curing effect, as compared with a control group in which a 1.0% (w/v) HCO-60 solution was used.

The results are shown in Table 4.

TABLE 4

| Agent | Amount of Application[1] | Number of Specimens | Ulcer Index[2] | Improvement Ratio (%) |
|---|---|---|---|---|
| Control | 0 | 19 | 14.3 ± 1.3 | — |
| Tocopheryl retinoate | 1.56 | 20 | 13.7 ± 1.9 | 4.2 |
| Tocopheryl retinoate | 6.25 | 20 | 10.6 ± 0.9* | 25.9 |
| Ticiopheryl retinoate | 25.0 | 20 | 8.4 ± 0.9** | 41.3 |

Notes:
[1] mg/kg/one
[2] mm² mean value ± standard error
*, ** with significant difference (margin of error: p <0.05, p <0.01, resp.)

The test results on the effect on treatment of ulcer have revealed that tocopheryl retinoate provides the anti-ulcer effect at a single dose of 6.25 mg/kg.

3. Treatment of Ulcer (Part 2):

As the above test results above have shown the effectiveness of tocopheryl retinoate in a single dose of 6.25 mg/kg. Tocopheryl retinoate in a single dose of 6.25 mg/kg has been compared in the antiulcer activity with gefarnate (Trademark: GEFANIL), cetraxate hydrochloride (Trademark: NEUER), and cimetidine (Trademark: TAGAMET).

Doses of the tested agents are as shown in Table 2. They were administered in the form of a suspension with a 1.0% (w/v) of HCO-60 in the same manner as above.

The results are shown in Table 5 below.

TABLE 5

| Agent | Amount of Application[1] | Number of Specimens | Ulcer | Improvement Ratio (%) |
|---|---|---|---|---|
| Control | 0 | 38 | 7.7 ± 0.8 | — |
| Tocopheryl retinoate | 6.25 | 18 | 4.9 ± 0.7* | 36.4 |
| Gefarnate | 50 | 21 | 6.2 ± 0.9 | 19.5 |
| Cetraxate HCl | 300 | 16 | 11.2 ± 2.4 | 45.5 |
| Cimetidine | 100 | 31 | 5.4 ± 0.7* | 29.9 |

Notes:
[1] mg/kg/single dose
[2] mm² mean value ± standard error
*: with significant difference (margin of error: p <0.05)

As apparent from the test results, tocopheryl retinoate as active ingredient according to the present invention can exhibit remarkable antiulcer activity at lower doses compared with the other agents. It is thus to be understood that tocopheryl retinoate exhibits an excellent antiulcer effect on the basis of the potent tissue growth activity confirmed by the tests on the tissue growth activity as described in item I above.

III. Comparison of $ED_{30}$ Values for Rat's Acetic Acid Ulcer:

As apparent from the biological activity tests as described in items I and II above, it has been found that tocopheryl retinoate possesses a remarkable antiulcer effect. $ED_{30}$ values of tocopheryl retinoate for rat's aceticacid ulcer have also been reviewed by using therapeutic preparations. The results are described below.

1. Formulations for Preparations Containing Tocopheryl Retinoate:

Formulations for preparations to be used for the tests are as follows:

| Formulation No. 1: | |
|---|---|
| Tocopheryl retinoate | 100 mg |
| Light silicic anhydride | 106 mg |
| Highly viscous hydroxypropylcellulose | 100 mg |
| Magnesium stearate | 6 mg |
| Total | 312 mg |

This formulation contains highly viscous hydroxypropylcellulose in place of low substituted hydroxypropylcellulose as an essential ingredient (b) to be formulated in the antiulcer agent according to the present invention.

| Formulation No. 2: | |
|---|---|
| Tocopheryl retinoate | 100 mg |
| Magnesium metasilicate aluminate | 104 mg |
| Magnesium stearate | 4 mg |
| Total | 208 mg |

This formulation contains magnesium metasilicate aluminate as a pharmaceutically acceptable adsorbent, in place of light silicate anhydride to be used for the powdery material (a).

| Formulation No. 3: | |
|---|---|
| Tocopheryl retinoate | 50.0 mg |
| Light silicic anhydride | 55.0 mg |
| Ascorbic acid | 0.5 mg |
| Low substituted hydroxypropylcellulose | 20.0 mg |
| Corn starch | 36.5 mg |
| Polyvinyl pyrrolidone | 7.0 mg |
| Magnesium stearate | 6.0 mg |
| Total | 175.0 mg |

This formulation is identical to the formulation obtained in Example 1 above.

2. Methods:

By using a group of 20 rats, acetic acid ulcer was formed and tested in the same manner as have been described in item II above.

The $ED_{30}$ value is shown as a single dose in mg/kg necessary for improvement in an ulcer index by 30% in a control group of non-treatment on the basis of an ulcer index on day 14 after operation.

The $ED_{30}$ value as likewise determined for a group in which a 1.0% (w/v) suspension of tocopheryl retinoate in HCO-60. The $ED_{30}$ values for the tested formulations are determined and relative activity values for the Formulations Nos. 1 to 3 were given on the basis of the $ED_{30}$ value for the single formulation of tocopheryl retinoate being represented as 1.

3. Results:

The results are shown in Table 6.

TABLE 6

| Formulations | $ED_{30}$ Values[1] | Relative Activity Values |
|---|---|---|
| Single formulation of tocopheryl retinoate | 9.6 | 1.00 |
| Formulation No. 1 | 6.4 | 1.50 |
| Formulation No. 2 | 4.9 | 1.96 |
| Formulation No. 3 | 1.2 | 8.00 |

Note:
[1] mg/kg/single dose

As apparent from the above test results, it has now been found that the antiulcer agent according to the present invention (Formulation No. 3) comprise a unique combination of ingredients with an optional ingredient group. The agent possesses remarkably potent antiulcer activities. The unique combination of elements comprises (a) the powdery material which includes tocopheryl retinoate, light silicic anhydride and ascorbic acid or its derivative, (b) low substituted hydroxypropyl cellulose, and (c) polyvinylpyrrolidone. The optional ingredient group comprises additives.

IV. Antiulcer Effects:

It has been found from the test results obtained in item III above that the antiulcer agent according to the present invention based upon its unique formulation has shown excellent effects. It has been further reviewed whether these effects are more beneficial as compared to that of a group in which only tocopheryl retinoate is applied.

1. Methods:

The effect on rat's acetic acid ulcer was examined in the same manner as in the tests made in item II above.

2. Agents administered:

The formulations obtained in Example 1, on the one hand, were orally administered twice daily so as to allow a single dose of tocopheryl retinoate to amount to 1.56 mg/kg, 6.25 mg/kg, and 25.0 mg/kg, respectively.

A 1.0% (w/v) suspension of tocopheryl retinoate in HCO-60, on the other hand, was likewise administered orally in the same single dosage as above.

The latter was used as a control group, and ulcer indexes for the former were determined and improvement rates were also given on the basis of the ulcer index for the latter.

3. Results:

The results are shown in Table 7.

TABLE 7

| Agent | Amount of Application[1] | Number of Specimens | Ulcer Indexes[2] | Improvement Ratio (%) |
|---|---|---|---|---|
| Control | 0 | 19 | 14.3 ± 1.3 | — |
| Tocopheryl retinoate | 1.56 | 20 | 13.7 ± 1.9 | 4.2 |
| Tocopheryl retinoate | 6.25 | 20 | 10.6 ± 0.9* | 25.9 |
| Tocopheryl retinoate | 25.0 | 20 | 8.4 ± 0.9** | 41.3 |
| Antiulcer agents of the present | 1.56 | 20 | 9.5 ± 1.3** | 33.6 |
|  | 6.25 | 20 | 8.4 ± 0.7** | 41.3 |
|  | 25.0 | 20 | 6.0 ± 0.7** | 58.0 |

TABLE 7-continued

| Agent | Amount of Application[1] | Number of Specimens | Ulcer Indexes[2] | Improvement Ratio (%) |
|---|---|---|---|---|
| invention | | | | |

Notes:
[1] amounts translated into tocopheryl retinoate: mg/kg/single dose
[2] mm: mean value ± standard error
*, **: with significant difference (margin of error: p <0.05, p <0.01, resp.)

As apparent from the above test results, it is to be understood that, although tocopheryl retinoate shows an antiulcer effect when administered alone, the antiulcer agents according to the present invention exhibits more potent antiulcer activities in the same relative amounts than does single dose of tocopheryl retinoate.

Thus, it is noted that the antiulcer agents according to the present invention demonstrate particularly remarkable antiulcer effects and that the effects are based on unique formulations containing tocopheryl retinoate.

What is we claimed:

1. An anti-peptic ulcer composition for topical delivery of tocopheryl retinoate to the ulcerated lesion in the gastrointestinal tract which permits said tocopheryl retinoate to remain in contact with said lesion for a sufficiently prolonged period of time to effectively treat said ulcerated lesion, said anti-ulcer composition comprising a powdery mixture containing:
   (a) from about 0.05 to about 60 parts by weight tocopheryl retinoate absorbed on silicic anhydride having an average diameter of up to about 3.0 microns;
   (b) from about 5 to about 20 parts by weight low substituted hydroxypropylcellulose having not less than 5.0 percent and not more than 16.0 percent of hydroxypropoxy ($-OC_3H_6-OH$) groups calculated on a dried basis; and
   (c) from about 2 to about 15 parts by weight polyvinylpyrrolidone having a molecular weight of from about 30,000 to about 40,000.

2. A dosage unit of the anti-peptic ulcer composition of claim 1 in the form of a powder.

3. A dosage unit of the anti-peptic ulcer composition of claim 1 compressed into a tablet.

4. A dosage unit of the anti-peptic ulcer composition of claim 1 in the form of a capsule containing said anti-ulcer composition.

5. A dosage unit of the anti-peptic ulcer composition of claim 1 comprising granules of said anti-ulcer composition.

6. An anti-peptic ulcer composition of claim 1 wherein the amount of tocopheryl retinoate contained in the component (a) is from about 30 to about 60 percent by weight of the total amount of tocopheryl retinoate and said light silicic anhydride.

7. An anti-peptic ulcer composition for delivering tocopheryl retinoate to an ulcerated lesion of the stomach wall which permits said tocopheryl retinoate to be retained directly on said lesion for a sufficiently prolonged period of time to effectively treat said ulcerated lesion, said tocopheryl retinoate being in a powdery form comprising:
   (a) a silicic anhydride having an average diameter of up to about 3.0 microns on which said tocopheryl retinoate is adsorbed;
   (b) a low substituted hydroxypropylcellulose having not less than 5.0 percent and not more than 16.0 percent of hydroxypropoxy ($-OC_3H_6-OH$) groups calculated on a dried basis; and
   (c) a polyvinylpyrrolidone having a molecular weight of from about 30,000 to about 40,000,
wherein said low substituted hydroxypropylcellulose and said polyvinylpyrrolidone permit dispersion of said tocopheryl retinoate over the entire ulcerated lesion to be treated with said tocopheryl retinoate.

8. The anti-peptic ulcer composition of claim 1, including a pharmaceutically acceptable antioxidant.

9. The anti-peptic ulcer composition of claim 8, wherein the antioxidant is selected from the group consisting of ascorbic acid, derivatives of ascorbic acid or the pharmaceutically acceptable salt or ester thereof, and tocopherol.

10. A method of topically treating an ulcerated lesion of the gastrointestinal tract which comprises orally administering a powdery mixture comprising:
   (a) from about 0.05 to about 60 parts by weight tocopheryl retinoate adsorbed on silicic anhydride having an average diameter of up to about 3.0 microns;
   (b) from about 5 to about 20 parts by weight low substituted hydroxypropylcellulose having not less than 5.0 percent and not more than 16.0 percent of hydroxypropoxy ($-OC_3H_6-OH$) groups calculated on a dried basis; and
   (c) from about 2 to about 15 parts by weight polyvinylpyrrolidone having a molecular weight of from about 30,000 to about 40,000,
whereby the tocopheryl retinoate remains in contact with said ulcerated lesion for a sufficiently prolonged period of time to effectively treat said ulcerated lesion, and the tocopheryl retinoate is permitted to work directly on said lesion for said prolonged period of time.

* * * * *

UNITED STATES PATENT AND TRADEMARK OFFICE
CERTIFICATE OF CORRECTION

PATENT NO.  :  5,039,699

DATED       :  August 13, 1991

INVENTOR(S) :  Masaaki KURIHARA et al.

It is certified that error appears in the above-identified patent and that said Letters Patent is hereby corrected as shown below:

On the cover page of the patent, in the Assignee data, insert the following after "Tokyo, Japan":

-- and Nisshin Flour Milling Co., Ltd., Tokyo, Japan --.

Signed and Sealed this

Twenty-third Day of February, 1993

*Attest:*

STEPHEN G. KUNIN

*Attesting Officer*   Acting Commissioner of Patents and Trademarks